United States Patent [19]

Hopkins

[11] 4,216,185
[45] Aug. 5, 1980

[54] METHOD AND APPARATUS FOR PURGING DISINFECTING HIGH PURITY WATER DISTRIBUTION SYSTEMS

[76] Inventor: Dale W. Hopkins, P.O. Box 2611, New Bern, N.C. 28560

[21] Appl. No.: 951,714

[22] Filed: Oct. 16, 1978

Related U.S. Application Data

[63] Continuation-in-part of Ser. No. 850,644, Nov. 11, 1977, abandoned.

[51] Int. Cl.² .............................. A61L 1/00; A61L 3/00; A61L 13/06; A61L 13/00
[52] U.S. Cl. ........................................ 422/28; 137/115; 137/240; 210/63 Z; 210/64; 210/194; 210/195.1; 422/37; 422/116; 422/243; 422/291

[58] Field of Search .................... 21/61; 137/115, 240; 210/63 Z, 64, 194, 195 R; 422/37, 28, 291, 243, 116

[56] References Cited

U.S. PATENT DOCUMENTS

| | | | |
|---|---|---|---|
| 1,531,808 | 3/1925 | Parkinson | 210/181 |
| 3,019,185 | 1/1962 | Fouilland et al. | 210/64 X |
| 3,448,045 | 6/1969 | Hess et al. | 210/64 X |
| 3,549,528 | 12/1970 | Armstrong | 210/64 X |

*Primary Examiner*—Barry S. Richman
*Attorney, Agent, or Firm*—Clifton T. Hunt, Jr.

[57] ABSTRACT

High purity water distribution systems are purged and disinfected by incorporating an outlet purge line into the conventional recirculating loop of the prior art. The purge line communicates with each outlet opening of the high purity water system and means are provided for intermittently and sequentially purging the outlets.

19 Claims, 3 Drawing Figures

METHOD AND APPARATUS FOR PURGING DISINFECTING HIGH PURITY WATER DISTRIBUTION SYSTEMS

CROSS-REFERENCE TO OTHER APPLICATIONS

This application is a continuation-in-part of application Ser. No. 850,644, filed Nov. 11, 1977 entitled A METHOD FOR EFFICIENT $H_2O$ DISTRIBUTION PURGING AND DISINFECTION and now abandoned.

BACKGROUND OF THE INVENTION

The invention is useful in a piping system for distribution of high purity water to stabilize the purity of water or other fluid at or above a predetermined level. High purity water is only one fluid with which the invention may be used. It may also find utility maintaining a desired level of purity of other fluids in a piping system.

It has long been recognized that high purity water, which has less than one (1) part per million contamination as total matter and a bacteria count of less than one (1) colony per milliliter, is useful in performing certain test procedures in the medical arts and in research in other fields. By comparison, ultra-pure water is recognized as having less than one tenth (0.1) part per million contamination as total matter and less than one colony of bacteria per 100 milliliters. It has also been recognized that contamination occurs rapidly when the fluid remains static in the piping system. It is therefore standard practice in high purity water distribution systems to have a reservoir of water with the desired minimum solids content and which is chlorinated to destroy bacteria and to pump water from the reservoir to a distribution loop of the high purity water system. The main loop is connected to a plurality of individually controlled outlets and the water is constantly circulated through the distribution loop to be available at each outlet when needed. A treatment unit is included within the distribution loop through which the water is constantly circulated to keep the water in the main loop at the desired level of purity. The repurified water flowing through the distribution loop at all times is not as subject to contamination as is static water.

As is well known in the prior art, the material from which the piping is formed plays an important part in maintaining the water at a desired level of purity. Glass tubing has been found less than ideal because of the soluble inorganic materials present to some degree in all glass. Metal piping also gives off an undesirable amount of soluble inorganic solids. Plastic tubing offers the best material for delivering high purity water from a source of supply to the distant outlet. Teflon has been recognized as one of the most satisfactory plastics but because of its cost is used only in cases where other materials are not satisfactory for the desired purity of the water. Polyethylene and polypropylene tubing has been found satisfactory for the average high purity water system.

Even with the proper plastic material for piping and even with water being constantly pumped around the distribution loop and through the treatment unit, there remains a continuing source of contamination in the high purity piping systems of the prior art. That is found in the branch lines which extend between the distribution loop and the individual outlets spaced around the loop. Bacteria develop in the static water in branch lines whose outlets are not used for an hour or more. The bacteria inhabit the tiny recesses and openings in the walls of the tubing and in the connections which join the tubing together. The bacteria multiply in the static water in the branch line and migrate into the distribution loop and contaminate the water in the distribution loop before it is drawn from a downstream outlet. The prior art provides for effective disinfection of the water at the treatment unit in the distribution loop, but that often occurs only after the contaminated water has been innocently used at an outlet between a static branch line and the treatment unit, which might destroy the usefulness of an important project.

According to the prior art the branch lines and their outlets were purged manually by the users of the water with long purge times often resulting in an inadequate quality of purity. Timely manual purging is impractical and unreliable. The use of a continuous purge of these branch distribution lines and their outlets has been determined to be impractical due to increased pumping/energy cost especially where numerous outlets are employed. The routing of the main recirculating distribution loop by each outlet is not practical because of the increased length of the piping in the recirculating loop, which results in increased piping cost and consequently higher discharge pressures at the recirculating pump for maintenance of adequate fluid velocity. Yet, static pipe recontamination inevitably occurs without timely and systematic purging of the branch lines and their outlets.

SUMMARY OF THE INVENTION

The invention utilizes the distribution loop of the prior art with its treatment unit and continuous circulation and incorporates into the distribution loop a purge line equipped with automated valving and controls to allow systematic sequential purging at preset intervals of the branch lines and outlets in the system. Sequential purging, that is limiting the number of outlets that are open at any one time, is required to maintain acceptable distribution fluid pressure and reduce system pumping/energy demand. It is an object of this invention to enable efficient and controlled purging of numerous outlets without increasing recirculation flow rates or pumping and energy demands beyond those normally associated with the prior art.

The invention also includes means for disinfecting the water on a different cycle than the intermittent purging of the branch lines and outlets. For example, the purging of the branch lines and outlets may occur every hour and the periodic disinfection as by chemical injection of such efficient disinfectants as ozone every 24 hours. The use of the purge/disinfect/purge procedure at adequate intervals enables a distribution piping system to convey high purity water with the requisite high purity piping materials several hundred feet and to supply a higher number of outlets than has heretofore been possible while maintaining the desired purity of the effluent.

According to the invention, the purge line may return the effluent to a reservoir for further treatment, which was not done in the prior art.

It is an object of this invention to incorporate into an existing distribution loop of a high purity water system a purge line which communicates with each outlet in the system and also communicates with a reservoir, whereby water may be transmitted through the branch lines and purge lines as desired.

It is another object of this invention to include within the branch lines and purge line appropriate valving and circuitry to enable the branch lines to be purged intermittently and sequentially.

Another object of the invention is to provide means for automatically introducing chemical disinfectant into the branch lines and purge line on a different cycle than the intermittent purging of these lines.

It is a more specific object of this invention to provide an apparatus of the type described wherein the effluent from the purge line may be introduced into a reservoir of the system for reuse through the system.

DETAILED DESCRIPTION OF THE INVENTION

Figure 1:
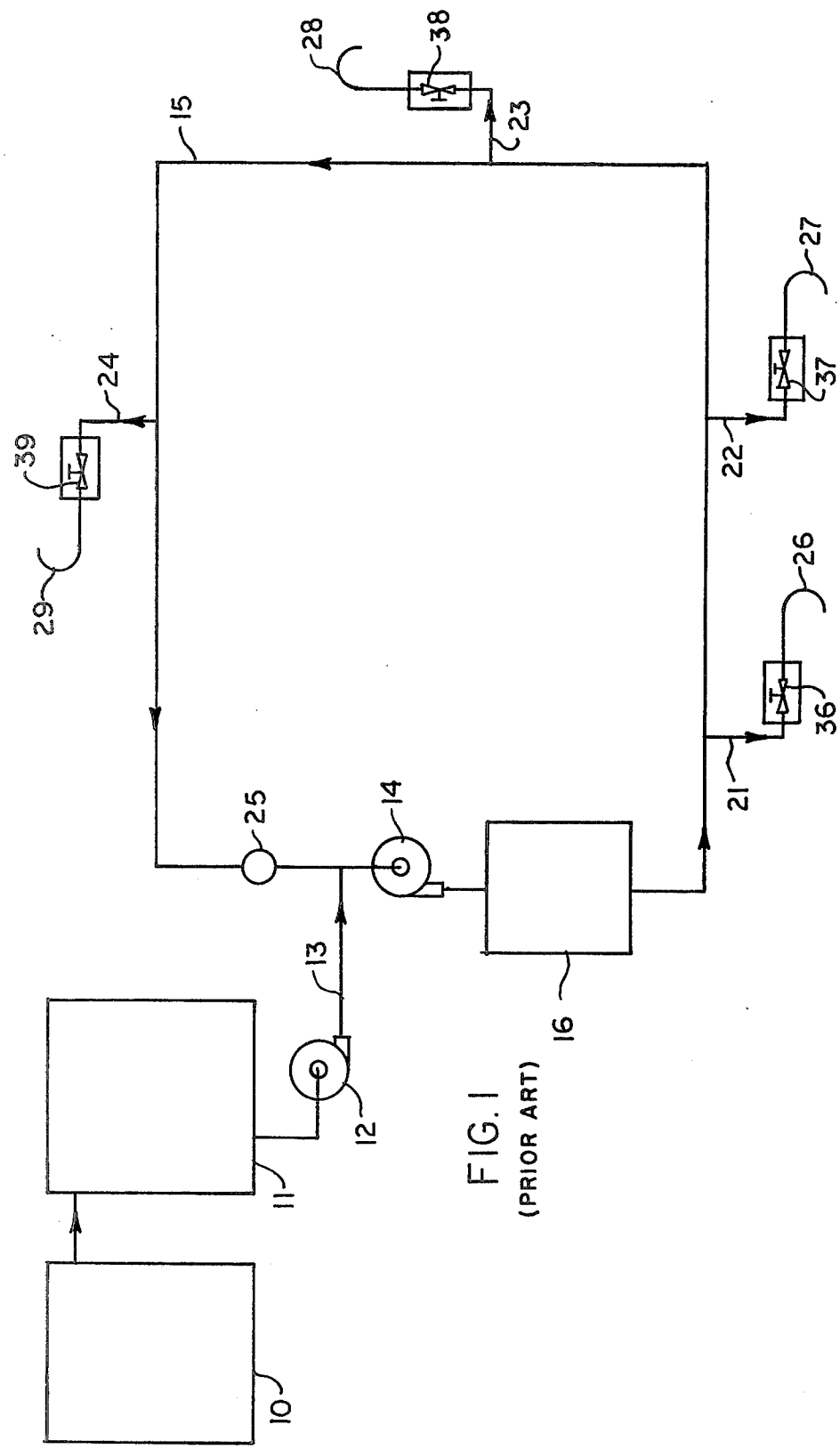
FIG. 1 is a somewhat schematic diagram of a prior art high purity fluid system illustrating how the effluent is delivered to outlets spaced along the distribution loop.

The invention will be described in connection with a high purity water system although the invention is equally useful with distribution systems for other high purity fluids and the invention is not limited to use with water.

The present invention is used with apparatus heretofore used in distribution systems for high purity water and an understanding of the prior art is useful in understanding the present invention. It is known that in the conveyance of high purity water within a distribution system the purity of the water at the outlet is dependent on several factors of which the following are the most important:

(1) the purity of the material in the piping;
(2) the length of time the fluid is in a static condition within the pipe;
(3) the number of infrequently used branch lines and their location in reference to the main distribution loop;
(4) microorganism contamination within the distribution system.

All of the factors affecting the purity of the fluid remain valid in the use of the present invention. The purity of the piping material is still important but not as critical as in the prior art. Plastic tubing is preferred, and an inexpensive plastic such as polypropylene and polyethylene can be successfully used in most applications where the present invention is employed. This is possible because of the extraction of trace contaminants from the piping material by the frequent purging and recirculation as carried out by this invention.

The total exposure time which a given volume of high purity water would be in contact with a given piping material in the prior art was determined by frequency of use. Those lines which were used more frequently and thereby subjected the fluid to less exposure to the piping material delivered the highest purity fluid at the outlet. In contrast those lines that were not used frequently and thereby resulted in greater exposure of the fluid to the piping material were sources of contamination and in large distribution systems the purity of the effluent at the end of the system was drastically reduced. Infrequently used lines also offer a residence for microorganism growth which, in time, spreads to the fluid in the distribution loop.

There are two basic classes of matter that contaminate water.
1. Organics
   (a) dissolved organic compounds which are soluble in water;
   (b) particulate organics such as carbon black, bacteria, etc.
2. Inorganics
   (a) The water soluble constituents of metals, salts, etc.

Other contaminants are colloidal organometallic compounds and dissolved gases. The degree and speed of water contamination depends on the solubility and concentration of the contaminant with which the water is in contact, the ambient conditions, and the water purity. Water is the universal solvent. Literally thousands of chemical combinations which make up or compose almost everything we see, use, and touch can be dissolved by water to some degree.

The more inert materials (those which exhibit the lowest water solubility) are usually chosen for high purity/ultra-pure water distribution piping. For example, glass is very pure organically but contains trace levels of inorganics throughout its structure. These inorganic elements are soluble in water in varying degrees. Water that contains higher levels of contaminants than the glass will not be appreciably contaminated by the glass. However, water which contains lower levels of contamination than the glass will be significantly contaminated by lengthy exposure.

Given the analytical capability which now exists there is no material that will not, to some detectable degree, contaminate either high purity or ultra-pure water. Teflon and glass are two of the most inert and best materials for the conveyance of high purity and ultra-pure water. However, cost and mechanical disadvantages present some problems in employing such materials. Polyethylene and polypropylene can be manufactured to reasonable purity levels at less than one-tenth the cost of Teflon or glass. All four of the above materials are suitable for high purity and ultra-pure water conveyance. Teflon and glass are better but more expensive than polyethylene and polypropylene.

This invention allows the use of polyethylene, for example, in the conveyance of high purity and ultra-pure water and provides higher purity water at the outlet than can be achieved with use of either Teflon or glass materials in the prior art distribution system of FIG. 1. This improved performance is accomplished by periodically purging the branch distribution lines by moving water that may have been contaminated by static conditions and piping materials extractables to lower pressure areas for disinfection, removal of dissolved solids and reuse. This purging of branch lines and outlets in the case of high purity and ultra-pure water distribution results in a continual cleaning or purifying of the piping system due to the higher purity fluids (water) extraction of trace matter from the pipe material's surfaces. While this extraction of trace matter from piping materials is inevitable in any high purity and ultra-pure water distribution system, the present invention effectively controls the rate of extraction and the removal of extracted materials from the water for economical water reuse. The degree to which this is accomplished by the invention is not possible by any other known economical means.

The above statement may seem to be contradictory. How can the extraction of contaminants from piping materials by water and the consequent contamination of the water be useful in maintaining high or ultra-purity of the water, especially when, as used here, the word "extraction" means purification of the piping by transferring trace materials from the piping materials to the water and resulting in water contamination? In the prior art, extraction and recontamination of high purity and ultra-pure water was an uncontrolled occurence which resulted in low quality of water at the outlet.

According to the invention, the extraction process is greatly increased by controlled purging of the branch distribution lines and outlets. The controlled extraction (removal of piping materials soluble contaminants) by high purity or ultra-pure water purifies the piping materials gradually, ultimately reducing water recontamination potential and improving the quality of water at the outlets. In addition to the chemical extraction capabilities of the invention it has been demonstrated that fluid velocities above two feet per second are effective in producing the turbulence necessary for efficient disruption and purging of microorganisms from plastic piping. It is the nature of several types of microorganisms to attach themselves as colonies on the surface of piping materials if allowed to proliferate undisturbed. The infestation increases with time to the point that it cannot be easily removed by water flow but often requires an aggressive disinfectant for correction. The invention through frequent, controlled, and turbulent flow effectively prevents microorganism infestation of distribution piping.

The importance of periodic chemical disinfection to multiple outlet high purity water distribution systems cannot be over emphasized, however, it is the maintenance of frequent, controlled, and turbulent flow that minimizes recontamination of the distribution of high purity water low in microorganisms and pyrogens. The controlled reduction in water recontamination reduces organic extractables also, which are a requirement for bacteria (microorganism) growth and proliferation. A reduction of the dissolved organics contained in water will always directly reduce the growth potential for microorganisms. The degree of purification of piping materials which can be effected by the invention is dependent on the purity of the water leaving the treatment station in the main distribution loop; station 16 in FIG. 2. The higher the water purity, the higher the capability of pipe purification. The highest extraction rates are produced when the water is at maximum purity (free of contaminants to be extracted), with extraction capability sharply decreasing as contaminant equilibrium is approached. The frequent and controlled replacement of contaminated water with higher purity water greatly enhances the rate of trace contamination extraction and pipe purification.

The present invention incorporates means for insuring that the water in all lines is frequently removed and repurified according to a predetermined schedule. With a purge cycle of once an hour and an interval of one minute the same degree of pipe purification can, for example, be obtained in approximately thirty (30) days that would normally require two and a half (2½) years with average usage.

Referring to the prior art system illustrated in FIG. 1, a solids reduction system 10 comprising any known means for reducing water contaminants to an acceptable level for the high purity water system, such as reverse osmosis, ultrafiltration, distillation, deionization and any other desired means provides high purity water of an acceptable level to a reservoir 11 where it is stored for use in the distribution system. The high purity effluent from the reservoir may be repressurized by a pump 12 to provide adequate distribution pressure throughout the system or a gravity feed may be utilized wherever feasible. The pump 12 or a gravity feed delivers the high purity effluent from the reservoir 11 through a feed line 13 to a distribution loop 15. A pump 14 is mounted in distribution loop 15 for delivery of the high purity effluent through a treatment station 16 and past branch lines 21, 22, 23 and 24 and through a check valve 25 back to the inlet side of the pump 14. Pump 14 moves effluent continuously through the distribution loop 15.

The branch lines 21, 22, 23 and 24 each provide communication between the distribution loop 15 and respective outlets faucets 26, 27, 28 and 29. Flow of effluent from outlets 26, 27, 28, 29 is controlled by respective valves 36, 37, 38 and 39.

When, for example, outlet 26 is used infrequently the branch line 21 supplying outlet 26 contains static water even though water flows continuously through distribution loop 15. Bacteria begin to proliferate within branch line 21 in a matter of minutes. The size of the bacteria colony can become great enough to move into the distribution loop 15 with consequent degradation of the fluid in loop 15 and at downstream outlet 27 and the succeeding downstream outlets in the distribution loop before the water is returned through pump 14 to treatment station 16 where the unacceptable contaminated water would be adequately treated by known means to restore the purity of the water to an acceptable level. In the meantime, however, the purity of the water had been undesirably lowered unknown to the operator of the outlet 27 and possibly destroying the reliability or usefulness of a valuable project.

Figure 2:
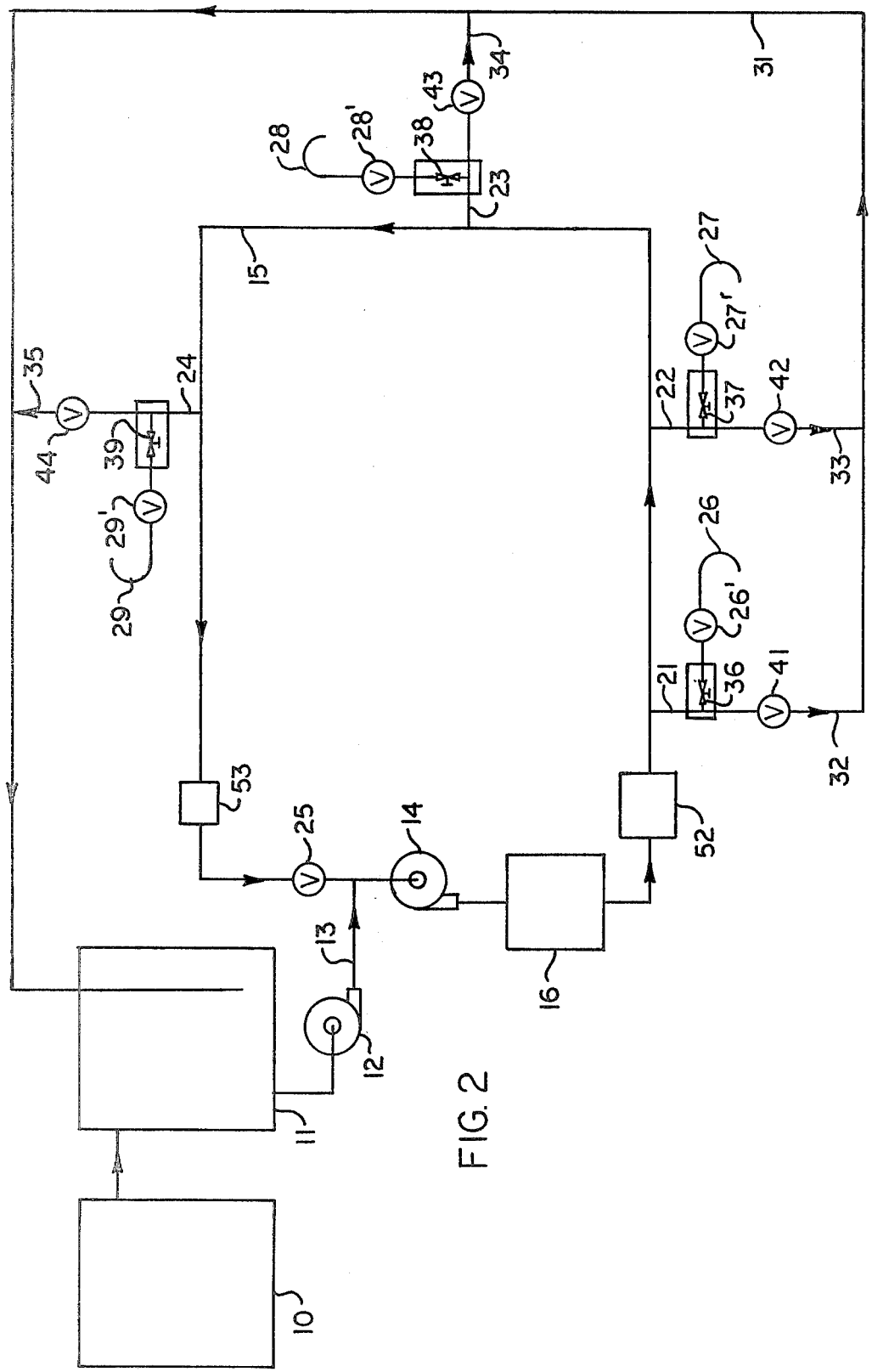
FIG. 2 is a view similar to FIG. 1 but showing the incorporation of the purge line of this invention in the prior art high purity fluid distribution system.
Figure 3:
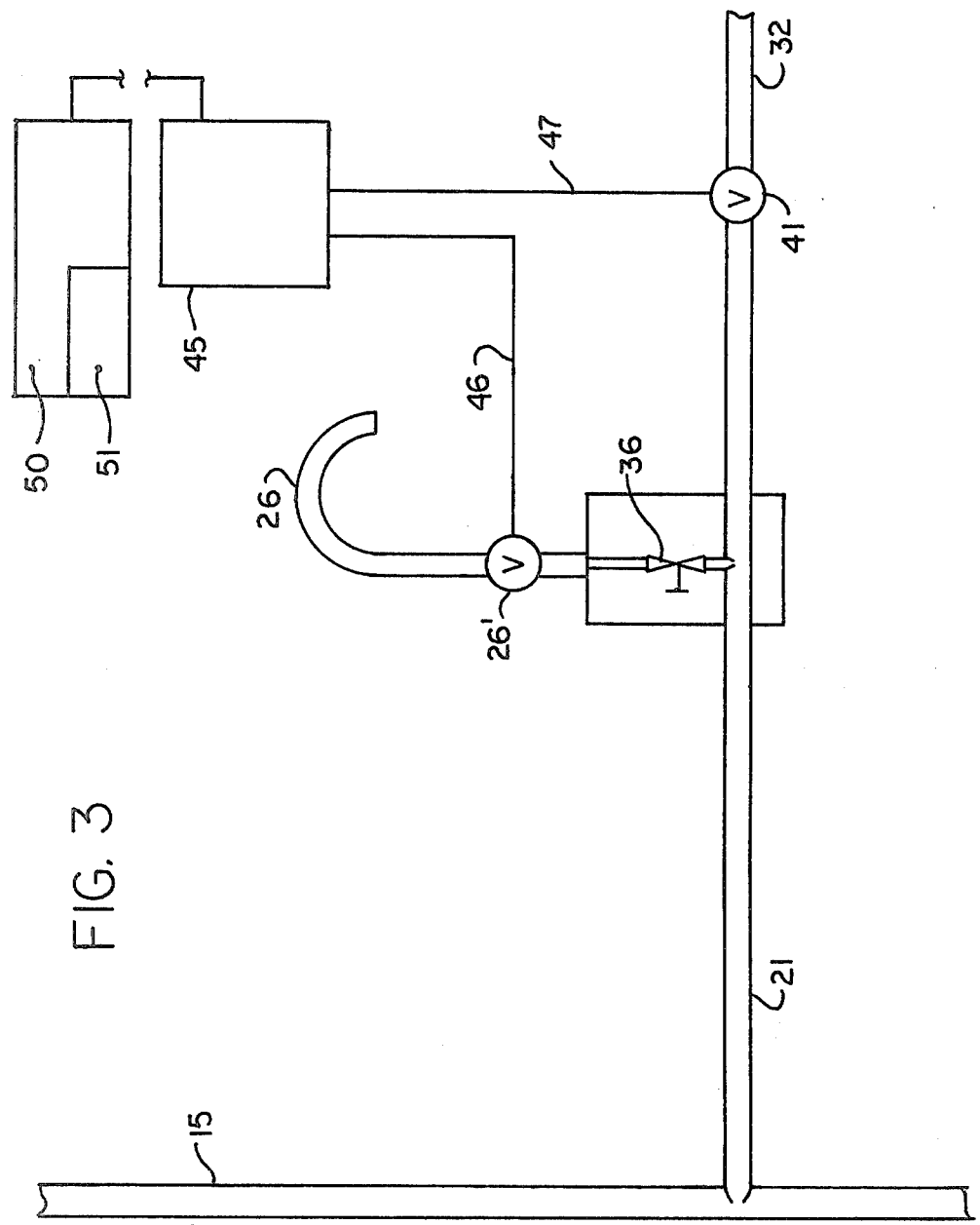
FIG. 3 is a schematic view of a laboratory faucet outlet illustrating the valving and controls which cooperate with the purge line to enable intermittent purging of the outlets.

The invention as illustrated in FIGS. 2 and 3 allows for the intermittent purging of the branch lines 21–24, either manually or automatically. A purge line 31 extends outwardly of the main distribution loop 15 and includes purge branches 32, 33, 34 and 35 establishing communication between respective branch lines 21–24 and purge line 31, which is illustrated as terminating in reservoir 11 but which may, with suitable valving, return the water to distribution line 15 downstream of the last outlet in distribution line 15. Purge branches 32–35 communicate with respective branch lines 21–24 at the juncture of the branch lines with respective outlets 26–29. Regulating valves 36–39 are provided in respective outlets 26–29 for manually controlling the flow rate of fluid to be delivered through respective outlets 26–29. Purge valves 26'–29' are installed in respective outlets 26–29 and purge valves 41–44 are installed in respective purge branches 32–35. The purge valves are selectively operable to purge respective outlets 26–29 and respective branch lines 21–24.

An outlet control station 45 is located in close proximity to outlet 26 and corresponding outlet control stations (not shown) are located in close proximity to the remaining outlets 27–29. Control lines 46 and 47 extend from the control station 45 to valves 26' and 41 associated with outlet 26, and corresponding control lines, not shown, extend between the remaining outlet control stations and their respective outlets 27' and 42, 28' and 43, 29' and 44 of the remaining outlets 27–29.

The control lines 46 and 47 for outlet 26 and the remaining control lines may comprise any well known mechanical or electrical structure for opening and closing the valves.

Each of the outlet control stations, such as illustrated at 45, includes mechanisms for sequentially opening its respective valves such as 41, 26' in FIG. 3 to sequentially purge branch lines such as 21 and outlets such as 26 in FIG. 3. Valves 41 and 26' may remain open for any desired length of time, it having been found effective in one instance for valve 41 in purge line 32 to remain open one minute to adequately purge branch line 21 and for valve 26' to thereafter remain open 15 seconds to purge outlet 26. The valves for purging the remaining branch lines 22–24 and outlets 27–29 will open sequentially for desired lengths of time.

Each outlet station control such as at 45 for outlet 26 in FIG. 3 is connected to a main control panel 50 which includes a timer 51. Each outlet control station will, when signalled by the main control panel, sequentially activate its purge valve (41–44) for one minute, for example, and then for a shorter length of time such as 15 seconds activate its outlet valve (25'–29'). The purge cycle may be initiated every hour, for example.

A chemical disinfection station 52 is preferably incorporated in the distribution loop 15 downstream of treatment unit 16 and in advance of the first branch line 21 to outlet 26. The disinfection station is responsive to the main control panel 50. Chemical disinfectant is infused intermittently into the effluent flowing continuously through distribution loop 15 and is coordinated by the main control panel with a purge cycle to provide maximum distribution of the disinfectant through the distribution loop 15, the branch lines 21–24 and outlets 26–29, and to provide adequate contact of the disinfectant with the piping.

The infusion of disinfectant into the system once every 24 hours is normally adequate and it should be coordinated with a purge cycle during a time when the high purity water system is not being used to avoid the inadvertent use of water containing the disinfectant. The main control panel 50 may include means for overriding the outlet control stations such as 45 during the disinfectant cycle to prevent the use of water containing the disinfectant. The length and frequency of the disinfectant cycle will vary as will the length and frequency of the purge cycle in distribution systems of varying size and materials, with subsequent purge cycles facilitating the removal of the disinfectant from the system.

The purging of the disinfectant and contaminant residuals after termination of a disinfection cycle is preferably monitored by sensor 53 in distribution loop 15 to indicate completion of the purge and disinfection cycle and reactivation of the outlet control panels such as indicated at 45 for outlet 26 in FIG. 3.

The piping design as described will facilitate the efficient purging and disinfection and continuing maintenance of high purity water distribution systems in such a manner that will allow high purity effluent to be supplied each outlet with less recontamination than has heretofore been possible.

Although specific terms have been employed in the specification and drawings, they are used in a descriptive sense only and not for purposes of limitation.

I claim:

1. A method of purging high purity water distribution systems having a reservoir, a distribution loop communicatively connected with the reservoir, a treatment unit in the distribution loop, a plurality of branch lines and outlet faucets arranged along the distribution loop, means for continuously circulating fluid through the distribution loop and means for selectively drawing off fluid from the distribution loop through the branch lines and their outlet faucets, said method comprising the additional step of selectively intermittently purging fluid from the branch lines independently of their outlet faucets.

2. A method according to claim 1 which includes the step of intermittently purging fluid from the outlet faucets.

3. A method according to claim 1 wherein the fluid purged from the branch lines independently of their outlet faucets is returned to the reservoir.

4. A method according to claim 1 wherein the branch lines are purged sequentially beginning with the upstream branch line.

5. A method according to claim 4 wherein the purging of each branch line is followed by the purging of its outlet faucet before the succeeding branch line is purged.

6. A method according to claim 1 wherein a chemical disinfection station is included in the distribution loop and wherein the method includes the additional step of coordinating the infusion of a disinfectant into the fluid in the distribution loop with a purge cycle.

7. A method according to claim 6 wherein the said additional step occurs once a day.

8. A method according to claim 1 wherein a purge cycle is initiated by purging a first branch line upstream of the remaining branch lines, said purge cycle including the steps of:
    (a) purging the outlet faucet connected to said first branch line,
    (b) then purging a succeeding branch line downstream of said first branch line,
    (c) purging the outlet faucet connected to said second branch line, and
    (d) repeating steps (b) and (c) on each successive downstream branch line and outlet faucet.

9. A method according to claim 8 wherein the purge cycle is initiated every hour.

10. A method according to claim 9 wherein the purge cycle includes purging each branch line about one minute and each outlet about fifteen seconds.

11. In a high purity water distribution system including a reservoir and a distribution loop having branch lines and outlet faucets for the delivery of high purity fluid from the reservoir to the outlet faucets, the combination of means for selectively intermittently purging the branch lines independently of their outlet faucets.

12. An apparatus as set forth in claim 11 wherein said purge cycles are initiated and terminated by a timer.

13. An apparatus according to claim 11 wherein means are provided for sequentially purging the branch lines beginning with the upstream branch line.

14. A structure according to claim 13 wherein means are provided for purging the outlet faucet of each branch line prior to the purging of the succeeding branch line.

15. An apparatus according to claim 11 wherein said means includes a purge line communicatively connected with each branch line.

16. An apparatus according to claim 15 and including means to cause water to flow intermittently from the distribution loop through the branch lines and into the purge line.

17. An apparatus according to claim 11 wherein the distribution loop includes a chemical disinfection station and wherein means are provided for infusing a disinfectant into the fluid in the distribution loop in coordination with a purging of the branch lines.

18. An apparatus according to claim 17 wherein the activation of the chemical disinfection station is coordinated with the activation of the means for purging the branch lines.

19. An apparatus according to claim 18 wherein said disinfection cycle and subsequent purging of disinfectant from the distribution system is monitored by a sensor.

* * * * *